United States Patent
Hermelin et al.

(10) Patent No.: US 6,375,956 B1
(45) Date of Patent: Apr. 23, 2002

(54) STRIP PACK (75) Inventors: Marc S. Hermelin, Glendale; Mitchell I. Kirschner, St. Louis; Sjoerd Osinga, Ellisville, all of MO (US)

(73) Assignee: Drugtech Corporation, Wilmington, DE (US)

(*) Notice: Subject to any disclaimer, the term of this patent is extended or adjusted under 35 U.S.C. 154(b) by 0 days.

(21) Appl. No.: 09/358,540

(22) Filed: Jul. 22, 1999

(51) Int. Cl.⁷ .................. A61K 9/00; A61K 9/14; A61K 9/20; A61K 9/48; B65D 83/04
(52) U.S. Cl. ............... 424/400; 424/464; 424/441; 424/466; 424/456; 424/489; 206/528; 206/531; 206/534; 206/538
(58) Field of Search ................. 424/423, 434, 424/435, 441, 436, 443, 449, 455, 456, 466, 489, 400, 464

(56) References Cited

U.S. PATENT DOCUMENTS

| | | | |
|---|---|---|---|
| 3,397,671 A | 8/1968 | Hartman et al. | 116/121 |
| 4,039,080 A | 8/1977 | Cappuccilli | 206/534 |
| 4,295,567 A | 10/1981 | Knudsen | 206/534 |
| 4,473,156 A | 9/1984 | Martin | 206/534 |
| 4,593,819 A | 6/1986 | Will | 206/538 |
| 4,736,849 A | 4/1988 | Leonard et al. | 206/534 |
| 4,749,085 A | 6/1988 | Denney | 206/534 |
| 4,817,819 A | 4/1989 | Kelly | 221/2 |
| 4,889,236 A | 12/1989 | Bartell et al. | 206/531 |
| 4,889,238 A | 12/1989 | Batchelor | 206/535 |
| 4,958,736 A | 9/1990 | Urheim | 206/531 |
| 5,109,984 A | 5/1992 | Romick | 206/531 |
| 5,265,728 A | 11/1993 | Allendorf et al. | 206/534 |
| 5,310,060 A | 5/1994 | Bitner | 206/532 |
| 5,325,968 A | 7/1994 | Sowden | 206/532 |
| 5,358,118 A | 10/1994 | Thompson et al. | 206/538 |
| 5,377,841 A | 1/1995 | Varon | 206/570 |
| 5,624,036 A | 4/1997 | Roulin et al. | 206/534 |
| 5,695,063 A | 12/1997 | Roulin et al. | 206/531 |
| 5,788,974 A | 8/1998 | D'Amico et al. | 424/405 |
| 5,830,490 A * | 11/1998 | Weinstein et al. | 424/405 |
| 6,077,530 A * | 6/2000 | Weinstein et al. | 424/451 |

* cited by examiner

Primary Examiner—James M. Spear
(74) Attorney, Agent, or Firm—Nath & Associates PLLC; Gary M. Nath

(57) ABSTRACT

The present invention relates to a disposable dispensing apparatus which provides optimal therapeutic support to humans and other animals by conveniently supplying a complex dosing regimen requiring simultaneous administration of storage-incompatible or unevenly dosed components in a shelf stable user-friendly format. The present invention is particularly useful for humans with special therapeutic needs, such as pregnant, lactating and/or menopausal women.

44 Claims, 6 Drawing Sheets

STRIP PACK

BACKGROUND OF THE INVENTION

1. Field of the Invention

The present invention relates to a disposable dispensing apparatus and method for providing nutritional and/or therapeutic agents to humans and other animals. In particular, the invention relates to a shelf-stable blister pack having a plurality of recesses designed to conveniently supply a dosing regimen requiring administration of storage-incompatible or unevenly dosed components.

2. Description of the Related Art

Physiological requirements vary from individual to individual and even within an individual during the course of a lifetime. Further, various conditions may effect physiological requirements. For example, pregnant, lactating and menopausal women may have enhanced needs for certain nutrients, therapeutic agents or treatments and reduced needs, or even tolerance, for other nutrients, therapeutic agents or treatments.

Meeting the specific physiological requirements of humans and other animals may require the use of a complex daily therapeutic regimen requiring administration of various biologically-active substances simultaneously or at different times during the day. Moreover, the complex daily therapeutic regimen may require simultaneous administration of biologically-active substances which may be storage-incompatible. Storage-incompatibility exists between two or more substances when the substances may not be formulated together in a single dosage unit or stored together in direct contact because the substances will interact in a negative manner. Storage-incompatibility also exists between two or more substances that cannot be formulated together in a single dosage unit because the sum total of the dosage amounts of the substances would result in a single dosage unit which is difficult to swallow or at least not optimal for swallowing. Storage-incompatibility also exists between two or more substances wherein at least one substance is a prescription substance and at least one substance is a non-prescription substance.

In addition the problem of simultaneous administration of storage-incompatible substances, complex daily therapeutic regimens also present the problem of poor patient compliance. In fact, according to medical literature, approximately 30% to 50% of all patients fail to comply with their physician's prescriptions. See Libow et al., *The Core of Geriatric Medicine: A Guide for Student and Practitioners*, 107 (1981). Interviews conducted with 178 elderly outpatients revealed that 59% are making errors in their medications and about 25% of the group as a whole averaged as many as 2.3 potentially serious errors per patient. See Schwartz et al., "Medication Errors Made by Elderly, Chronically Ill Patients", *American Journal of Public Health*, 52:2018–29 (1962).

Further, a study examining non-compliance in patients recently discharged from an acute care facility found that 50% of the patients deviated from the prescribed regime. See Parkin et al., "Deviation from Prescribed Drug Treatment After Discharge from Hospital", *British Medical Journal*, 2:686 (1976). Moreover, there is evidence that medication errors are an important factor in producing illness. See Seidl et al., "Studies on the Epidemiology of Adverse Drug Reactions", *The Bulletin of Hopkins Hospital*, 119:299–315, 1966.

There are a broad range of factors which play a role in poor patient compliance, including complexity of regimen, poor patient motivation, lack of sufficient knowledge on the part of the patient, memory loss and other cognitive dysfunctions, as well as attenuation of the special senses.

Disposable pharmaceutical containers for dispensing medicaments which are used to improve patient compliance have been previously disclosed. One type of pharmaceutical dispensing package arranges medicaments separately within individual recesses upon a planar card, forming a blister package. An example of such a package can be found in Knudsen, U.S. Pat. No. 4,295,567, which discloses a pharmaceutical dispensing container which holds two dosage units which are symptomatic treatment for respiratory tract disorders. The first of these dosage units being indicated for day-time administration and therefore being non-sedating. The second of these dosage units being indicated for night-time administration and therefore being sedating. Means of indication include dosage units being in register with a time chart and a distinguishing visible feature of the dosage units.

Thompson et al., U.S. Pat. No. 5,358,118, describe a stepped-edge blister pack for containing and dispensing units of doses of medication such as capsules, tablets, caplets or fast-dissolving dosage forms. The invention is comprised of a base sheet and a substantially planar lidding sheet. The base sheet has a plurality of blister compartments and a plurality of steps along its edges, one step being adjacent to each blister compartment. The substantially planar lidding sheet is peelably sealed to the base sheet except at extended edge regions, thus forming edge peel tabs. These edge peel tabs coincide with the steps along the edge of the base sheet, thus providing a series of finger accesses and thereby easing the process of opening each blister compartment. The lidding sheet is scored with lines of weakening, so that each blister compartment is removable from the blister package.

Sowden, U.S. Pat. No. 5,325,968, describes a package for holding tablets, which provides for limited entry into the package that is designed to be child proof. The user must complete a number of sequential steps in order to access the dosage. First, the user grips a trapezoidal section of an access tab to expose a finger depression. Next, the user grips a cover overlying the depression, which further extends over the dosage. Finally, the user pulls back this cover to reveal the dosage form.

Urheim, U.S. Pat. No. 4,958,736, describes a package for oral contraceptive tablets. The package contains four rows of seven tablets per row. Three adjacent rows contain active contraceptive tablets, while he fourth row contains placebo tablets. A line of severability is provided between the row placebo tablets and an adjacent row of active tablets, thereby enabling dispensing 21-day and 28-day oral contraceptive formulations using a single package.

Roulin et al., U.S. Pat. No. 5,695,063, describe a blister pack for pharmaceuticals containing a base with a plurality of recesses which are surrounded by a shoulder. A lid foil is attached to the shoulders. Removable contents such as a tablet, capsules, or ampoules reside in each of the recesses and may be removed therefrom by pressing the recess in question and penetrating the lid foil or by removing the lid foil over the recess. The blister pack features a movable lid or a clamping element which covers at least one recess, and the clamping element is arranged in such a manner that it can be slid over the lid foil, and the clamping element closes off again at least one recess where the lid foil has been penetrated or peeled back, or close again at least one lid which on filling was left untitled and without a lid.

D'Amico et al., U.S. Pat. No. 5,788,974, describe a pharmaceutical dispensing container which holds multiple dosage units for aiding in the compliance in the eradication/ treatment of *Helicobacter pylori* and subsequent/related gastric maladies on relation to said bacterial infection using a repetitive dosage regimen for a treatment period of sufficient duration to mitigate said bacterial infection formatted in such a way to gain ease of compliance resulting in improved outcome of treatment. Dosage units may be antibiotic, anti-microbial, or symptomatic relief agents in any combination.

Bartell et al., U.S. Pat. No. 4,889,236, describe a rigid, tripartite, credit card-style blister pack medication package, which is particularly useful for dispensing medications which must be taken on a calendar day schedule. The package is of discrete design and may be conveniently carried in a purse or billfold.

Roulin et al., U.S. Pat. No. 5,624,036, describe a blister pack without additional packaging for pharmaceuticals, having a base with a plurality of recesses that are surrounded by a shoulder and a lid foil attached to the shoulder, where removable contents are accommodated in the recesses and can be removed therefrom by pressing in the recess in question and penetrating the lid foil or by removing the lid foil over the recess and having an accompanying leaflet. The accompanying leaflet represents part of the blister pack and is situated within the confines of the blister pack, for example in a compartment in the base or in a gripping facility on one side of the blister pack.

Bitner, U.S. Pat. No. 5,310,060, describes a novel tamper-evident, child-resistant blister package for medicaments and non-medicaments which is difficult to open by young children and impaired adults. Because the blister package has pull tabs which are designed to be pulled away from, rather than towards, article receiving pockets which may be present in the blister package other than the article receiving pocket being accessed, a young child or user of the blister package can only access one article receiving pocket at a time, whether deliberately or inadvertently. The blister package of the invention is an attractive and inexpensive package for the merchandising of pharmaceutical and other products which is constructed in a manner which facilitates mass production.

This type of pharmaceutical dispensing package wherein medicaments are arranged separately within individual recesses upon a planar card, forming a blister package, may further be inserted into a container designed to protect and/or otherwise further precipitate dispensing of the medication is also known in the art. An example of such a package can be found in Leonard et al., U.S. Pat. No. 4,376,849, which describe a method and apparatus to store and aid in dispensing of calendar-oriented drugs. The apparatus is comprised of a carrier containing a plurality of pill-containing enclosures, which are arranged in rows. Numerical and/or alphanumerical indicia are associated with the enclosures so that each enclosure is associated with only one day in a calendar month. One or more additional enclosures in different rows may also be associated with the same calendar date. Corresponding indicia on the reverse side of the carrier aid in the determination of which enclosure(s) to open. The package also provides a visual indication of calendar days for which pills have not been used by the patient and in this way provides patient compliance information to the physician prescribing such drugs. This dispensing apparatus is particularly suited to the administration of calendar-oriented prescription drugs for the treatment of menopausal symptoms.

Allendorf et al., U.S. Pat. No. 5,265,728, describe an arrangement for retaining blister pack tablets, which comprises a container with at least a front cover and a rear cover with a blister pack sandwiched there between and visible through a window in the front cover. The blister pack includes indicia thereon indicating the order in which the tablets should be taken and the container includes a pointer identifying the first tablet in the array of tablets to be consumed. Preferably, the container includes a daily calendar in the form of a loop or cylinder which is movable with respect to the container so that a desired starting say can be selected by the user or prescriber. Preferably, the loop or cylinder is lockable at its selected position. In accordance with two embodiments of the invention, front and rear lids are pivoted to the front and rear covers, respectively, to conceal the blister pack until it is necessary to take a tablet.

Kelly, U.S. Pat. No. 4,817,819, describes a tablet container having a cover and sliding tray, which is used for dispensing birth control tablets for either a twenty-one day or twenty-eight day cycle. Normally, the tray does not slide completely out of the cover and is stabilized with respect thereto when open. The case resembles a cosmetic compact and is reusable in the once birth control tablets contained in the blister pack are used up, a new blister pack may easily be inserted.

Varon, U.S. Pat. No. 5,377,841, describes a package for sleep therapy including a box having cards with doses in the form of tablets or capsules thereon, some of which are sleep inducing medicine and some of which are placebos, and an audiogenic recording for inducing sleep.

Batchelor, U.S. Pat. No. 4,889,238, describes a medicament package for improving compliance with a therapeutic regimen. The therapeutic regimen involves a plurality of medications administered to a patient in a prescribed sequence and in accordance with specific intervals. The package includes a multiplicity of blister cards of generally uniform planar dimensions. The blister cards carry the medicaments in sequential order on the individual cards and from card to card. The blister cards being placed in a stacked array with the principle dimensions thereof oriented generally horizontally and arranged in order of use with the first to be used topmost. Also included is a base which houses the stack of blister cards. The base permits direct and unobstructed access to the uppermost blister card and limited access only to the edges of the blister cards. A lid is adapted to cover the base and a movable to an open position allowing access to the uppermost blister card. Each blister card generally contain indicia denoting the order and sequence when the contents of a particular blister cavity are to be consumed.

Hartman et al., U.S. Pat. No. 3,397,671, disclose a reminder-dispenser for pills and the like which includes a holder, a carrier to be held be the holder, a plurality of individually openable pill pockets on the carrier and indicia means associated with the holder for selective location relative to the carrier indicating the period of consumption of pills in respective pockets.

Romick, U.S. Pat. No. 5,109,984, describes a reusable, plastic medication dispensing containers for dispensing medication for a blister pack. The container includes a top, bottom and retaining frame that are molded from a one-piece plastic and hingeably connected one to the other.

Pharmaceutical dispensing packages wherein medicaments are arranged separately within individual recesses of a nondisposable apparatus are also known in the art. An example of such a package can be found in Denney, U.S. Pat. No. 4,749,085, which describes a rectangular, open-top shallow tray with enclosing side walls and has markings designating each day of the week equally spaced across the top. A set of individual compartments or pill boxes for each day of the week resting in the tray line with each of the designated days of the week and frictionally and removably held in place in the tray so that each of the set of pill boxes can be separately and individually removed from the tray whereby the user can conveniently carry prescribed medication for a given day separate from the other days of the week.

Martin, U.S. Pat. No. 4,473,156, describes an apparatus for accurately selecting, storing, and dispensing multiple varieties of pills at preselected time intervals such as morning, noon, evening and night, which also includes a separate pill container for each unique variety of pill to be dispensed. Each pill container is identified by a distinctive color or colors to indicate the time interval(s) during which the pills in it are to be dispensed. For example, each recess in the morning could be identified by the color red; at noon, at least yellow; in the evening, at least blue; and at night, at least black. Any particular container will, therefore, be identified by at least one and not more than four colors. A pill tray includes a plurality of pill holding compartments arranged in columns identified with each of the days of the week in a row, each row representing the time intervals, such as morning, noon, evening and night. Each pill holding compartment in the row representing morning is red, the row representing noon is yellow, the evening row is blue and the night row is black. The tray is loaded by putting one pill from each container in each of the compartments colored the same as one of the colors identifying that container. Sliding panels are provided as covers for each of the columns, and the patient can access the proper medication by uncovering the appropriate compartment at the appropriate time interval.

Will, U.S. Pat. No. 4,593,819, describes a rectangular tray configuration having an array of open-topped compartments, which serves to hold a supply of medication arranged day by day and by time of taking. Associated with the tray is a support base having provision for storage of medication containers. A case may be provided for the tray and includes a cover to permit the tray to be carried without danger of the pills moving from the individual compartments.

Cappuccilli, U.S. Pat. No. 4,039,080, describes a tray having individual compartments for holding pills, capsules, or similar solid medication, each compartment being rectangular in plan view and arranged in a rectangular format or seven columns and a plurality of rows. The tray may be load with a weeks worth of medication for an individual patient with indicia adjacent to each column indicating the day of the week, and indicia adjacent to each row indicating the time of day each compartment is to be taken. A lid or cover cooperates with the wall means defining the individual compartments to mutually isolate the compartments when in the closed position. The inner surfaces of the compartments are preferably rounded in at least one plane to facilitate ease of tablet removal.

The above discussed holders, dispensers and pharmaceutical packages are deficient in several respects. Significantly, none of the above references present a convenient, simple and effective way of facilitating the simultaneous administration of storage-incompatible substances, particularly when said substances are taken as part of a complex sequential daily therapeutic regimen. Further, none of the above references specifically addresses a way to facilitate simultaneous administration of prescription and non-prescription substances as part of a complex regimen. Moreover, none of the above references addresses the issue of optimizing therapeutic support for humans and other animals. Therefore, there remains a need for a simple, inexpensive and convenient means for providing optimal therapeutic support for humans and other animals, and in particular for providing optimal support for humans and other animals having special therapeutic needs.

SUMMARY OF THE INVENTION

The present inventive subject matter is directed to a storage stable, disposable dispensing apparatus and method which provides optimal therapeutic support while overcoming the deficiencies of currently available pharmaceutical packages in a simple, effective, convenient and cost-efficient manner.

One embodiment of the present inventive subject matter is a storage stable, disposable dispensing apparatus for providing optimal therapeutic support to an animal by increasing compliance with a complex dosing regimen, which could include a prescription substance and a nonprescription substance during one dosing interval and facilitating simultaneous administration of storage-incompatible substances, said apparatus comprising: a blister pack having a plurality of predetermined areas, each of said predetermined areas defining a first recess and a second recess; a first dosage unit occupying the first recess, said first dosage unit comprising a first biologically-active substance; a second dosage unit occupying the second recess, said second dosage unit comprising a second biologically-active substance; a day indicia could be provided on said blister pack, said day indicia corresponding to each of said predetermined areas to increase patient compliance with said complex dosing regimen by indicating which day the dosage units are to be administered; wherein the complex dosing regimen requires simultaneous administration of said first and second biologically-active substances; said first biologically-active substance being storage-incompatible with said second biologically-active substance; and wherein said first recess and said second recess provide shelf stability by independently isolating in close proximity said first dosage unit and said second dosage unit to prevent interaction between the first and second biologically-active substances while facilitating simultaneous administration of said substances.

Another embodiment of the present inventive subject matter relates to a storage stable, disposable dispensing apparatus for increasing patient compliance with taking at least one prescription therapeutic substance through proximity and conjoint accessibility with at least one nonprescription substance; said apparatus comprising a storage stable blister pack having at least one row of a plurality of predetermined areas, each area defining at least one recess; a first dosage unit occupying at least one recess of at least one of said predetermined areas, said first dosage unit containing a nonprescription substance; a second dosage unit occupying at least one recess of at least one of said predetermined areas, said second dosage unit containing a prescription therapeutic substance, said second dosage unit arrayed with said first dosage unit on said blister pack adjacent to said second dosage unit; a day indicia provided on said blister pack, said day indicia corresponding to at least one of said predetermined areas; and wherein each of said predetermined areas has a seal that is independently accessible, removable or breakable.

An alternative embodiment of the present inventive subject matter is a storage stable, disposable dispensing apparatus for increasing patient compliance with taking at least one prescription therapeutic substance through proximity and conjoint accessibility with at least one nonprescription substance, said apparatus comprising a storage stable blister pack having at least one row of a plurality of predetermined areas, each area defining at least one recess; a first dosage unit occupying at least one recess of at least one of said predetermined areas, said first dosage unit containing a nonprescription substance; a second dosage unit occupying at least one recess of at least one of said predetermined areas, said second dosage unit containing a prescription therapeutic substance, said second dosage unit arrayed with said first dosage unit on said blister pack adjacent to said second dosage unit; a day indicia provided on said blister pack, said day indicia corresponding to at least one of said predetermined areas; and wherein said row of a plurality of predetermined areas has a seal that is independently accessible, removable or breakable.

Yet another embodiment of the present inventive subject matter is a storage stable, disposable dispensing apparatus for increasing patient compliance with taking at least one prescription therapeutic substance through proximity and conjoint accessibility with at least one nonprescription substance, said apparatus comprising a storage stable blister pack having at least one row of a plurality of predetermined areas, each area defining at least two recesses; a first dosage unit occupying a first recess of a first predetermined area and containing a nonprescription substance; a second dosage unit occupying a second recess of said first predetermined area and containing a prescription therapeutic substance, said second dosage unit arrayed with said first dosage unit on said blister pack adjacent to said second dosage unit; a day indicia provided on said blister pack, said day indicia corresponding to at least one of said predetermined areas; and wherein each of said predetermined areas has a seal that is independently accessible, removable or breakable.

A further embodiment of the present inventive subject matter is a storage stable, disposable dispensing apparatus for increasing patient compliance with a daily therapeutic regimen through proximity and conjoint accessibility with a multiplicity of therapeutic components which are to be administered concurrently, which comprises a blister pack having at least one row of a plurality of predetermined areas, each area defining at least two recesses; a first dosage unit occupying a first recess of a first predetermined area and containing a first therapeutic substance; a second dosage unit occupying a second recess of said first predetermined area and containing a second therapeutic substance; said second dosage unit arrayed with said first dosage unit on said blister pack adjacent to said second dosage unit; a day indicia provided on said blister pack, said day indicia corresponding to at least one of said predetermined areas; and wherein each of said predetermined areas has a seal that is independently accessible, removable or breakable.

A still further embodiment of the present inventive subject matter is a storage stable, disposable dispensing apparatus for increasing patient compliance with a daily therapeutic regimen through proximity and conjoint accessibility with a multiplicity of therapeutic components which are to be administered concurrently, which comprises: a storage stable blister pack having at least one row of a plurality of predetermined areas, each area defining at least two recesses; a first dosage unit occupying a first recess of a first predetermined area and containing a first therapeutic substance; a second dosage unit occupying a second recess of said first predetermined area and containing a second therapeutic substance; said second dosage unit arrayed with said first dosage unit on said blister pack adjacent to said second dosage unit; a day indicia provided on said blister pack, said day indicia corresponding to at least one of said predetermined areas; and wherein each of said predetermined areas has a seal that is independently accessible, removable or breakable.

An even further embodiment of the present inventive subject matter is a storage stable, disposable dispensing apparatus for increasing patient compliance with taking at least one prescription substance through proximity and conjoint accessibility with at least one nonprescription substance, said apparatus comprising a storage stable blister pack having at least one row of a plurality of predetermined areas, each area defining at least one recess; a first dosage unit occupying at least one recess of at least one of said predetermined areas, said first dosage unit containing a prescription substance may be a hormone replacement agent, a contraceptive agent, an osteoporotic agent, a chemotherapeutic agent, an anti-infective agent, an analgesic, a steroid, an appetite suppressant, a weight loss agent, a tobacco antagonist, an cholesterol reducer and combinations thereof; a second dosage unit occupying at least one recess of at least one of said predetermined areas, said second dosage unit containing a prescription therapeutic substance, said second dosage unit arrayed with said first dosage unit on said blister pack adjacent to said second dosage unit; a day indicia provided on said blister pack, said day indicia corresponding to at least one of said predetermined areas; and wherein each of said predetermined areas has a seal that is independently accessible, removable or breakable.

Another embodiment of the present inventive subject matter is a disposable dispensing apparatus for providing optimal therapeutic support to an animal by increasing compliance with a complex dosing regimen and facilitating administration of uneven doses of a biologically-active substance, said apparatus comprising: a blister pack having at least two rows of a plurality of predetermined areas; a first row of predetermined areas, each of the predetermined areas defining a first recess adapted to receive a first dosage unit, said first row of predetermined areas having a first time indicia; a second row of predetermined areas, each of the predetermined areas defining a first recess adapted to receive a second dosage unit, said second row of predetermined areas having a second time indicia; and wherein the first dosage unit has a greater or lesser amount by weight of the biologically active than the second dosage unit.

Yet another embodiment of the present inventive subject matter is a disposable dispensing apparatus for providing optimal therapeutic support to an animal by increasing compliance with a complex dosing regimen and facilitating administration of uneven doses of at least one biologically-active substance, said apparatus comprising: a blister pack having at least two rows of a plurality of predetermined areas; a first row of predetermined areas, each of the predetermined areas defining a first recess adapted to receive a first dosage unit, said first row of predetermined areas having a first time indicia; a second row of predetermined areas, each of the predetermined areas defining a first recess adapted to receive a second dosage unit, said second row of predetermined areas having a second time indicia; and wherein the first dosage unit is larger by volume than, smaller by volume than, or a different shape from the second dosage unit.

Another embodiment of the present inventive subject matter is a method for providing optimal therapeutic support to an animal by increasing compliance with a complex dosing regimen and facilitating simultaneous administration of storage-incompatible substances, which comprises: providing a blister pack having a plurality of predetermined areas, each of said predetermined areas defining a first recess and a second recess; providing a first dosage unit occupying the first recess, said first dosage unit comprising a first biologically-active substance; providing a second dosage unit occupying the second recess, said second dosage unit comprising a second biologically-active substance; providing day indicia on said blister pack, said day indicia corresponding to each of said predetermined areas to increase patient compliance with said complex dosing regimen by indicating which day the dosage units are to be administered; administering said nonprescription therapeutic substance and said prescription therapeutic substance together from said blister pack to an animal when indicated by said day indicia; wherein the complex dosing regimen requires simultaneous administration of said first and second biologically-active substances; said first biologically-active substance being storage-incompatible with said second biologically-active substance; and wherein said first recess and said second recess provide shelf stability by independently isolating in close proximity said first dosage unit and said second dosage unit to prevent interaction between the first and second biologically-active substances while facilitating simultaneous administration of said substances.

An alternative embodiment of the present invention is a method of increasing patient compliance with prescription therapeutic substances, which comprises providing a blister pack having at least one row of a plurality of predetermined areas; providing a first dosage unit containing a nonprescription substance in a recess in one predetermined area; providing a second dosage unit containing a prescription therapeutic substance in a recess in said blister pack such that said second dosage unit is located adjacent to said first dosage unit; providing indicia on said blister pack corresponding to said first and second dosage units; and administering said prescription therapeutic substance and said nonprescription substance together from said blister pack to an animal at the time indicated by said indicia.

A further embodiment of the present invention is a method for increasing patient compliance with a daily therapeutic regimen, which comprises providing a blister pack having at least one row of a plurality of predetermined areas; providing a first dosage unit containing a prescription therapeutic substance in a recess in one predetermined area; providing a second dosage unit containing a nonprescription therapeutic substance in a recess in said blister pack such that said second dosage unit is located adjacent to said first dosage unit; providing indicia on said blister pack corresponding to said first and second dosage units; and administering said nonprescription therapeutic substance and said prescription therapeutic substance together from said blister pack to an animal at the time indicated by said indicia.

Additional features and advantages of the present invention are described in, and will be apparent from, the detailed description of the presently preferred embodiments.

DETAILED DESCRIPTION OF THE INVENTION

As used herein, "animal" refers to a human, mammal or any other animal.

"Biologically-active substance" refers to any substance or substances comprising a drug, active therapeutic substance, metabolite, medicament, hormone, steroid, vitamin, fatty acid, amino acid, sugar, carbohydrate, polypeptide or mineral, any substance used for treatment, prevention, diagnosis, cure or mitigation of disease or illness, any substance which affects anatomical structure or physiological function, or any substance which alters the impact of external influences on an animal, or metabolite thereof, and as used herein, encompasses the terms "active substance", "therapeutic substance", "agent", "active agent", "active therapeutic agent", "drug", "medication", "medicine" "medicant" and the like, without limitation.

"Complex dosing regimen" refers to systematic administration of multiple dosage units at designated times during the day including, without limitation, administration of multiple dosage units which are potentially confusing to a patient.

"Uneven dosing" or "unevenly dosed" refers to doses of a biologically-active substance wherein each dose following the initial dose contains a different amount of biologically-active substance than the previous dose, including without limitation conventional external administration of each individual dose by a patient or a health/medical professional, or internal administration through controlled variable or pulsed release systems well known to persons of skill in the art, or combinations thereof. "Dose" refers to each individual release of substance into body tissue.

"Shelf stability" or "storage stability" refers to the ability of a substance to resist degradation or alteration in chemical, physical or biological properties while awaiting use during a period at least six months.

"Storage-incompatible substances" refers to substances that may not be formulated together in a single dosage unit or stored together in direct contact because the substances will interact in a negative manner and also substances that cannot be formulated together in a single dosage unit because the sum total of the dosage amounts of the substances would result in a single dosage unit which is too large to be swallowed. The term also refers to substances which may be stored in direct contact, however, one of the substances is preferably formulated in a dosage form which is either not preferred or incompatible with the other substance. Storage-incompatibility also refers to two or more substances wherein at least one substance is a prescription substance and at least one substance is a non-prescription substance.

"Storage-incompatibility" refers to the state that exists between storage-incompatible substances, as defined above.

The apparatus of the invention is a storage stable disposable dispensing apparatus which provides optimal therapeutic and/or nutritional support to an animal by increasing compliance with a complex dosing regimen and facilitating administration of storage-incompatible substances, and in particular, simultaneous administration of storage-incompatible substances. The present apparatus incorporates various types of blister packs. The blister packs are characterized by a plurality of single compartments referred to herein as "recesses". Each recess accommodates a dosage unit and isolates that dosage unit from other dosage units. In this manner, the biologically-active substance within each dosage unit will not come into contact with the biologically-active substance of the other dosage units, despite being in close proximity to other dosage units on the blister pack. This arrangement, particularly when incorporating day and time indicia corresponding to said recesses, eases simultaneous administration of storage-incompatible substances as required by a complex dosing regimen which provides optimal therapeutic support.

Figures 1A, 1B, 1C:
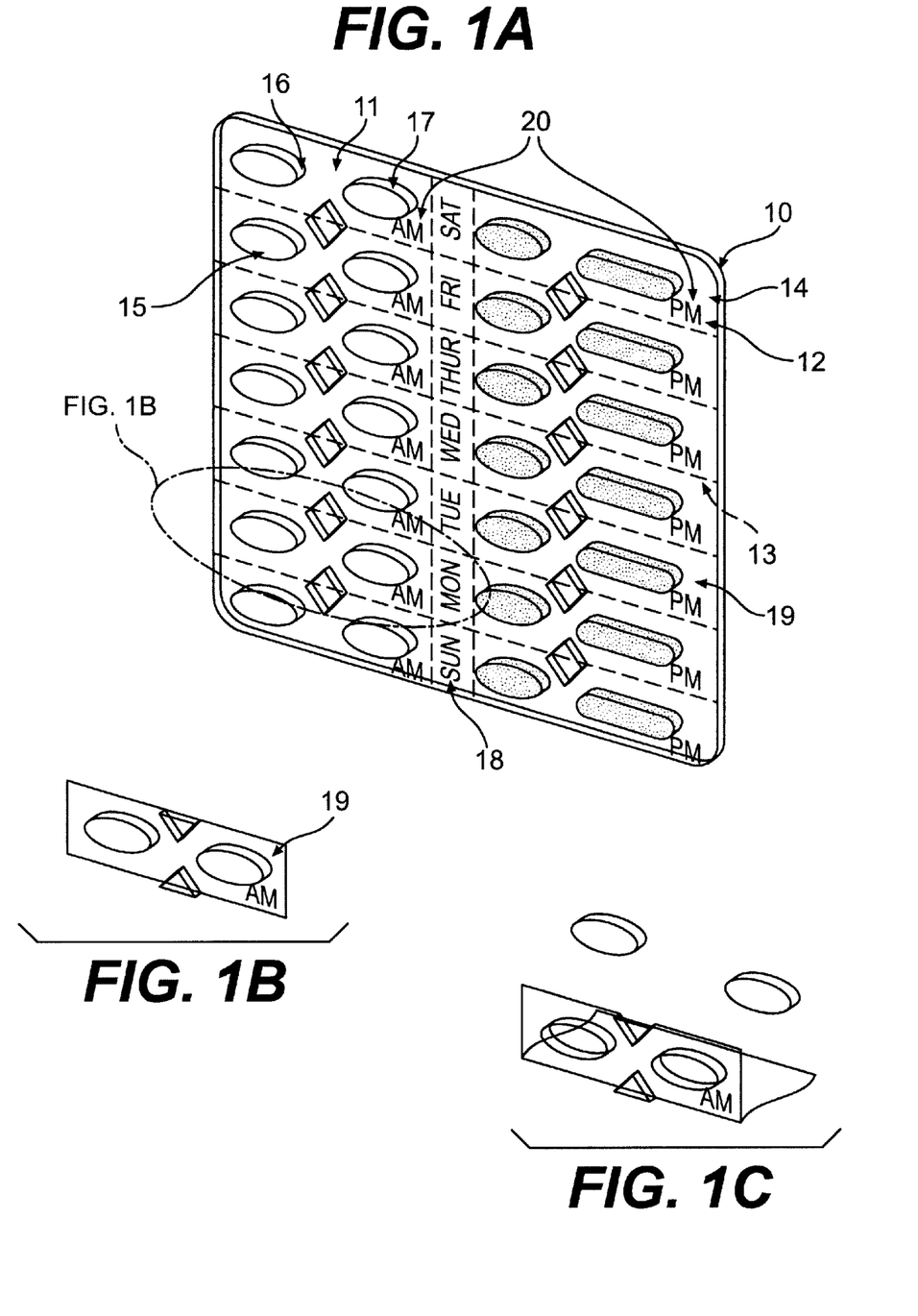
FIG. 1A is a top elevational view of the disposable, dispensing apparatus, illustrating specific display indicia according to an embodiment of the present inventive subject matter.
FIG. 1B is a cut-away top elevational view of one predetermined area.
FIG. 1C is a cut-away top elevational view of one predetermined area after the backing is removed.

FIG. 1A shows a novel disposable, dispensing apparatus for providing optimal therapeutic support to an animal by increasing compliance with a complex dosing regimen and facilitating simultaneous administration of storage-incompatible substances, in accordance with one embodiment of the inventive subject matter. Shown in FIG. 1A is a top elevational view of a blister pack 10 in which the lid foil 11 is joined at the shoulders 12 to the base 14. The lid foil 11 covers a plurality of recesses 15. Two adjacent recesses are contained within each predetermined area 19. Each predetermined area is separated from the other predetermined areas by perforated edges 13. Within each individual recess is a dosage unit 16, 17. In the area of the shoulders 12, the lid foil 11 is joined to the base 14, for example, by sealing or adhesive bonding (not shown). The recesses 15 are arranged in four columns and seven rows. The two interior columns are separated by a strip of sequentially ordered day indicia 18. The interior vertical edge of each predetermined area is bordered by the strip of sequentially ordered day indicia. Each day indicia indicates a day of the week. Within each row, the dosage units in the two recess which are in a predetermined area each contain a biologically-active substance which is storage-incompatible with a biologically-active substance in the dosage unit in the other recess of that predetermined area. For example, dosage unit 16 contains a biologically-active substance which is storage-incompatible with dosage unit 17. Time indicia 20 are provided on each predetermined area to show time of administration.

FIG. 1B shows a cut-away top elevational view of one of the predetermined areas described in FIG. 1.

Figure 2:
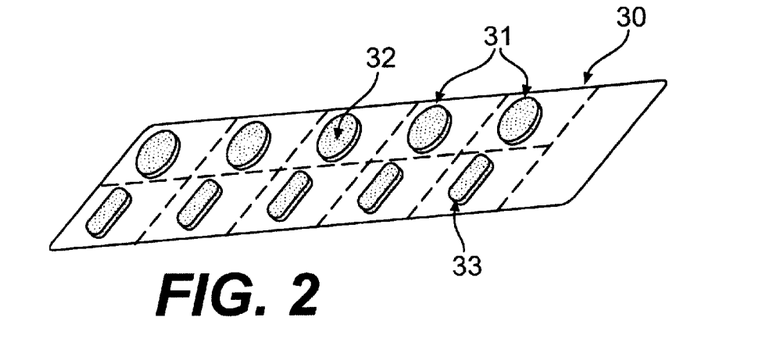
FIG. 2 is a perspective view of the disposable dispensing apparatus, showing alignment of a soft gelatin capsule and a tablet for simultaneous administration according to an embodiment of the present inventive subject matter.

FIG. 2 shows a novel disposable, dispensing apparatus for providing optimal therapeutic support to an animal by increasing compliance with a complex dosing regimen and facilitating simultaneous administration of storage-incompatible substances, in accordance with one embodiment of the invention. Shown in FIG. 2 is a perspective view of a blister pack 30 The blister pack 30 has a plurality of recesses 31. The recesses 31 are arranged in two columns and five rows. Within each individual recess is a dosage unit 32, 33. Within each recess of one column the dosage unit is a tablet 32. Within each recess of the other column the dosage unit is a soft gelatin capsule 33. Thus, within each row, the dosage units in the two recess which are in a predetermined area each contain a biologically-active substance which is storage-incompatible with a biologically-active substance in the dosage unit in the other recess of that predetermined area. For example, dosage unit 32 contains a biologically-active substance which is storage-incompatible with a biologically-active substance in dosage unit 33.

Figure 3:
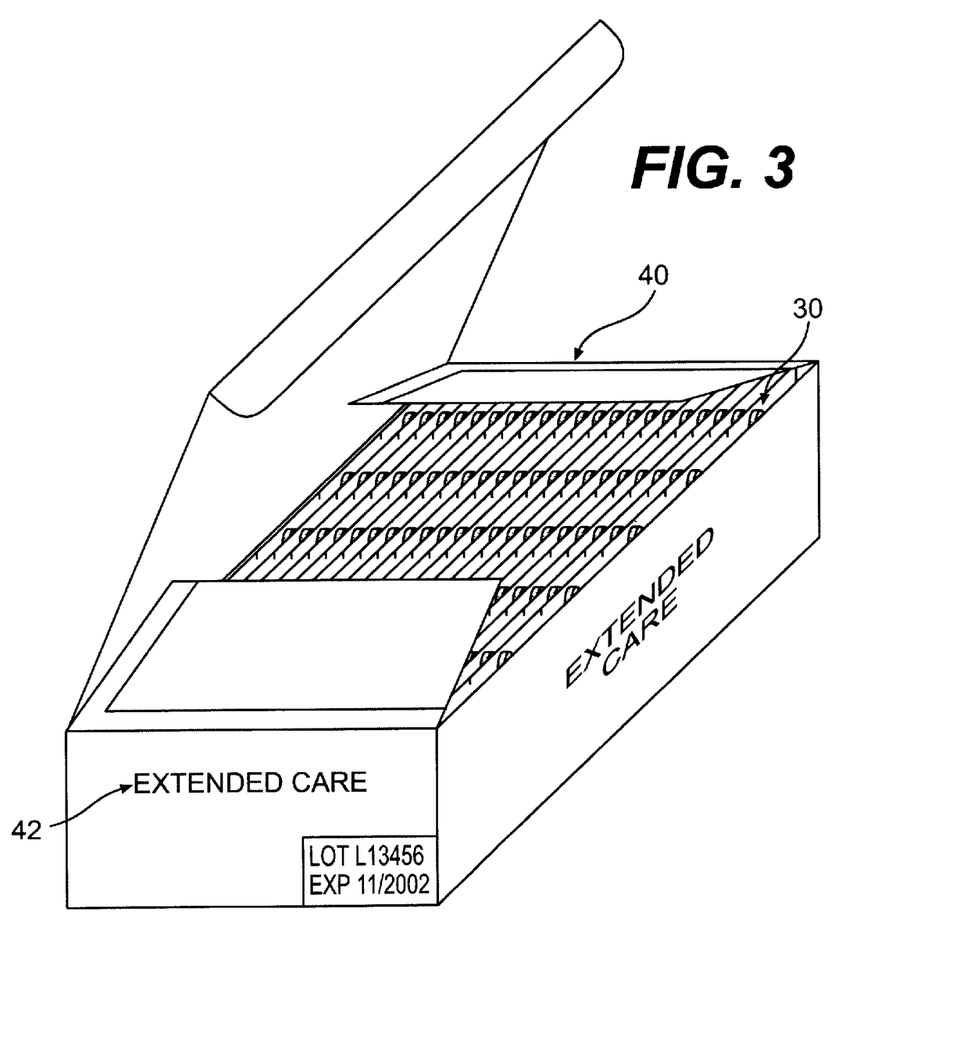
FIG. 3 is a perspective view of a storage container for storing a plurality of blister packs according to an embodiment of the present inventive subject matter.

FIG. 3 shows a storage container 40 for long term storage of a multitude of blister packs 30, as depicted in FIG. 2. The storage container 40 also incorporates indicia 42 which identify the product. Within the storage container or on the exterior of the container, instructions for use of the product may be provided (not shown).

Figure 4:
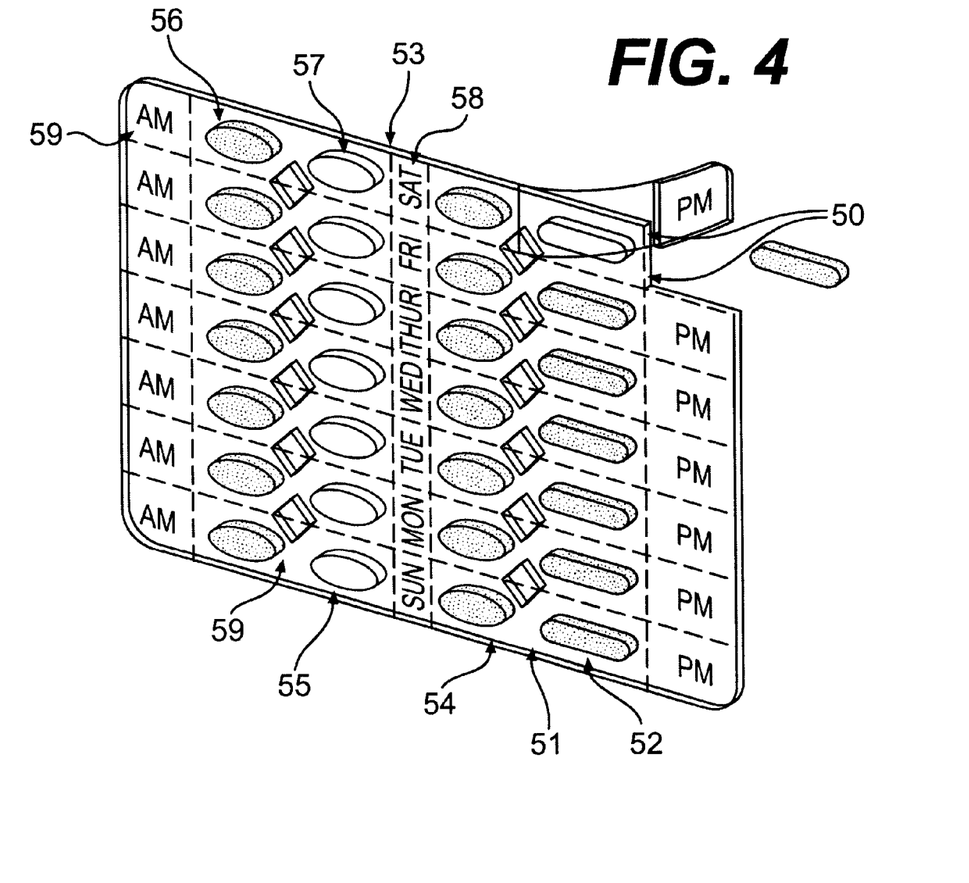
FIG. 4 is a top elevational view of the disposable dispensing apparatus, illustrating specific display indicia with pull-tabs according to an embodiment of the present inventive subject matter.

FIG. 4 shows a modified blister pack 50 which provides optimal therapeutic support to an animal by increasing compliance with a complex dosing regimen and facilitating simultaneous administration of storage-incompatible substances, in accordance with one embodiment of the inventive subject matter. Shown in FIG. 4 is a top elevational view of the blister pack 50 in which the lid foil 51 is joined at the shoulders 52 to the base 54. The lid foil 51 covers a plurality of recesses 55. Two adjacent recesses are contained within each predetermined area 59. Each predetermined area is separated from the other predetermined area by perforated edges 53. Within each individual recess is a dosage unit 56, 57. In the area of the shoulders 52, the lid foil 51 is joined to the base 54, for example, by sealing or adhesive bonding (not shown). The recesses 55 are arranged in four columns and seven rows. The two interior columns are separated by a strip of sequentially ordered day indicia 58. Each day indicia indicates a day of the week. Within each row, the dosage units in the two recess which are in a predetermined area each contain a biologically-active substance which is storage-incompatible with a biologically-active substance in the dosage unit in the other recess of that predetermined area. For example, dosage unit 56 contains a biologically-active substance which is storage-incompatible with dosage unit 57. Within each row, separate pull-tabs 59 each cover the lid foil 51 on the side of the lid foil opposite the base 54 in the region of each of said predetermined areas and extending beyond the exterior border of the base. In the area of the shoulders 52, the lid foil 51 is joined to each pull-tab 59, for example, by sealing or adhesive bonding (not shown). In this manner, at the appropriate time, the pull-tabs may be peeled away from the foil covering each of the directly adjacent recesses which contain the dosage units intended for simultaneous administration, as depicted in FIG. 4.

Figure 5:
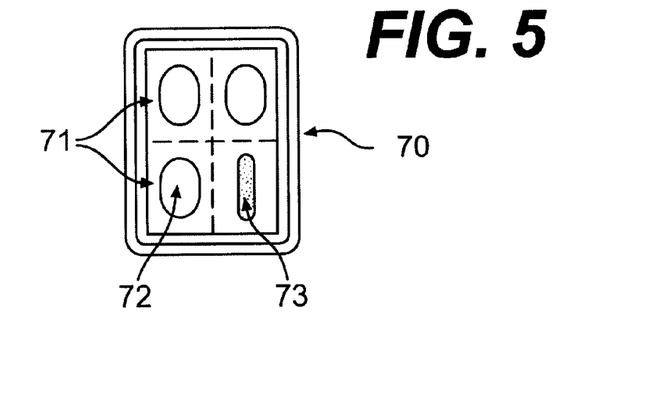
FIG. 5 is a top elevational view of the disposable dispensing apparatus, showing alignment of a soft gelatin capsule and three tablets for simultaneous administration according to an embodiment of the present inventive subject matter.

FIG. 5 shows a novel disposable, dispensing apparatus for providing optimal therapeutic support to an animal by increasing compliance with a complex dosing regimen and facilitating simultaneous administration of storage-incompatible substances, in accordance with one embodiment of the invention. Shown in FIG. 5 is a perspective view of a blister pack 70 The blister pack 70 has a plurality of recesses 71. The recesses 71 are arranged in two columns and two rows. Within each individual recess is a dosage unit 72, 73. Within one recess, the dosage unit is a tablet 72. Within each of the other recesses, the dosage unit is a soft gelatin capsule 73. Thus, within the individual blister packs, the dosage unit in the recess of one column contains a biologically-active substance which is storage-incompatible with a biologically-active substance in dosage unit in the adjacent recess. For example, dosage unit 72 contains a biologically-active substance which is storage-incompatible with dosage unit 73.

Figure 6:
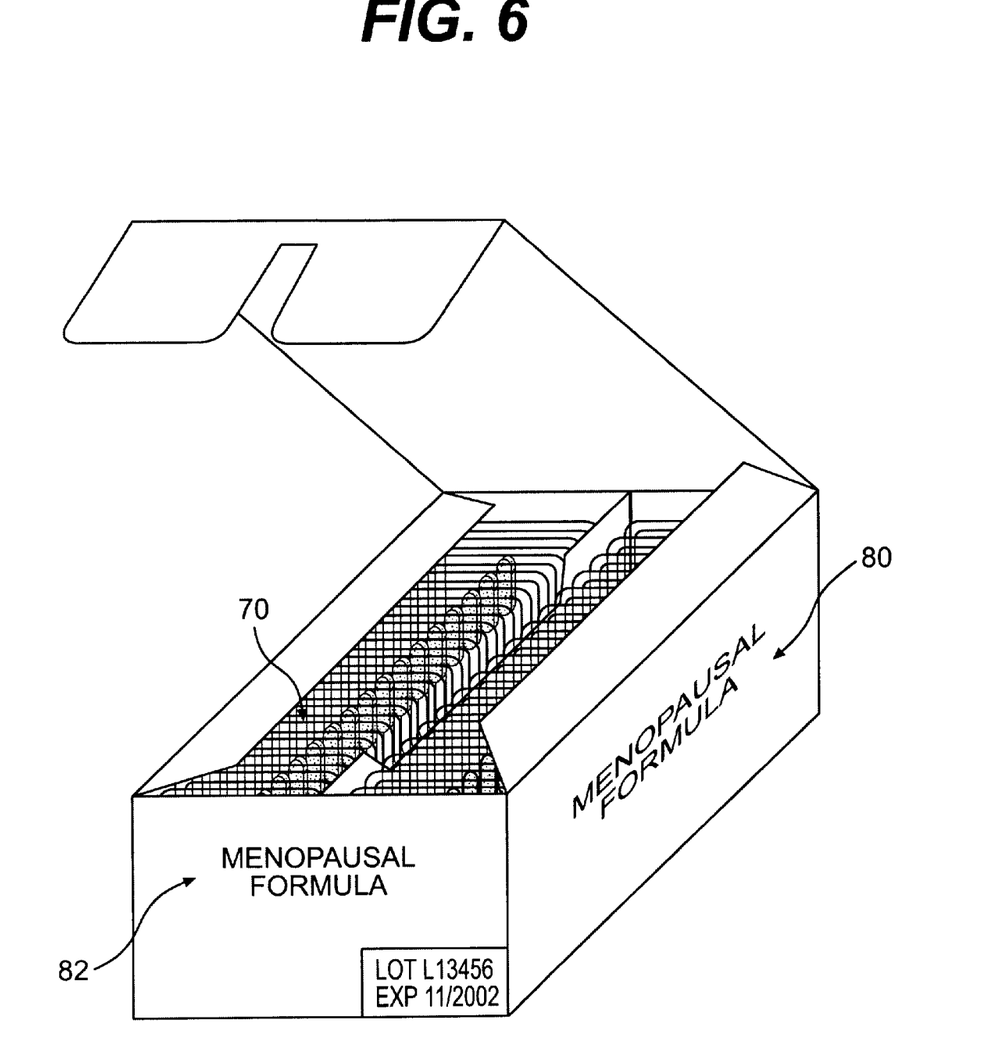
FIG. 6 is perspective view of a storage container for storing a plurality of blister packs according to an embodiment of the present inventive subject matter.

FIG. 6 shows a storage container 80 for long term storage of a multitude of blister packs 70 as depicted in detail in FIG. 5. The storage container 80 also incorporates indicia 82 which identify the product. Within the storage container or on the exterior of the container, instructions for use of the product may be provided (not shown).

Figure 7A:
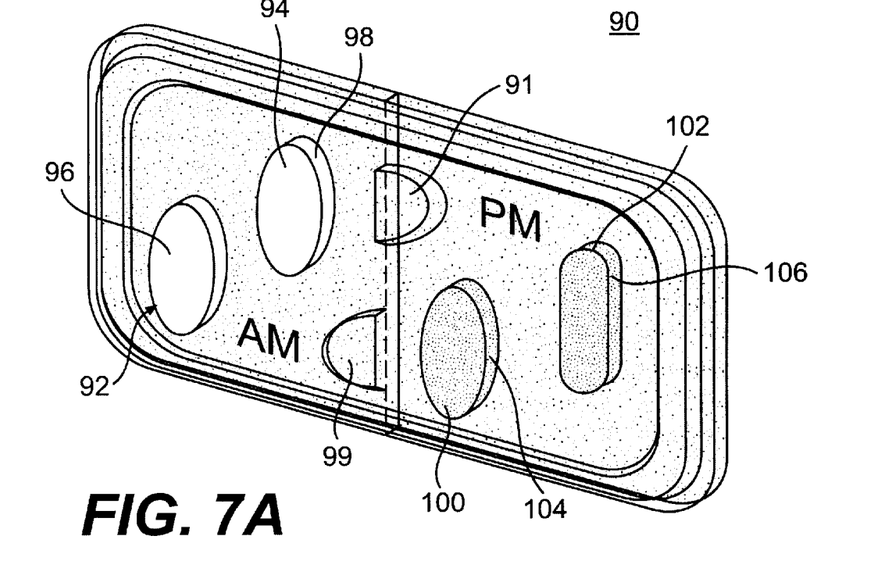
FIG. 7A is a perspective view of the disposable dispensing apparatus, showing alignment of a soft gelatin capsule and a tablet for simultaneous administration according to an embodiment of the present inventive subject matter.
Figure 7B:
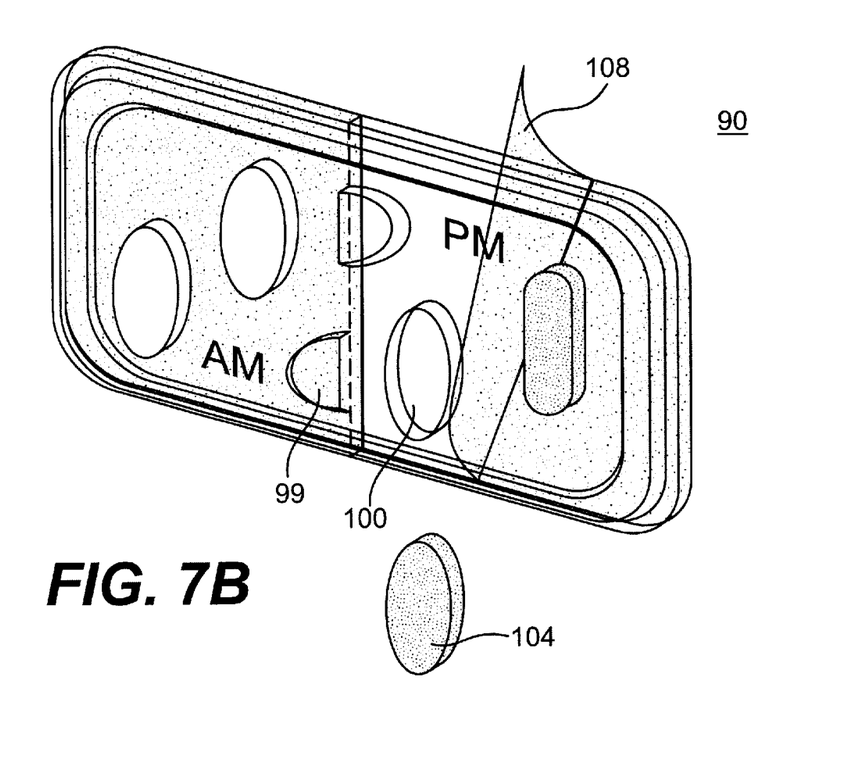
FIG. 7B is a perspective view of the disposable dispensing apparatus with a removable seal being partially removed.

FIGS. 7A and 7B show an alternate embodiment of a novel disposable, dispensing apparatus for providing optimal therapeutic support to an animal by increasing compliance with a complex dosing regimen and facilitating simultaneous administration of storage-incompatible substances.

Shown in FIG. 7A is a perspective view of a blister pack 90. Blister pack 90 is divided into an AM section for morning dosages and a PM section for evening dosages.

The AM section of blister pack 90 has a tab 91 and two recesses 92 and 94. Within recess 92 is a tablet 96 made up of a biologically-active substance and within recess 94 is a tablet 98 also made up of a biologically-active substance. The biologically-active substance of tablet 96 is storage-incompatible with the biologically-active substance of tablets 98. Therefore, by storing tablets 96 and 98 in separate recesses 92 and 94, respectively, the biologically-active storage-incompatible substances of tablets 96 and 98 are prevented from interacting with one another.

The PM section of blister pack 90 has a tab 99 and two recesses 100 and 102. Within recess 100 is a tablet 104 made up of a biologically-active substance and within recess 102 is a soft gelatin capsule 106 also made up of a biologically-active substance. The biologically-active substance of tablet 104 is storage-incompatible with the biologically-active substance of soft gelatin capsule 106. Therefore, by storing tablet 104 and soft gelatin capsule 106 in separate recesses 100 and 102, respectively, the biologically-active storage-incompatible substances of tablet 104 and soft gelatin capsule 106 are prevented from interacting with one another.

FIG. 7B shows blister pack 90 with a removable seal 108 partially removed through the use of tab 99 located at the center of blister pack 90. After removable seal 108 is removed tablet 104 and soft gelatin capsule 106 can be removed from recesses 100 and 102 respectively (note: FIG. 7B only depicts tablet 104 as being removed).

Figure 8A:
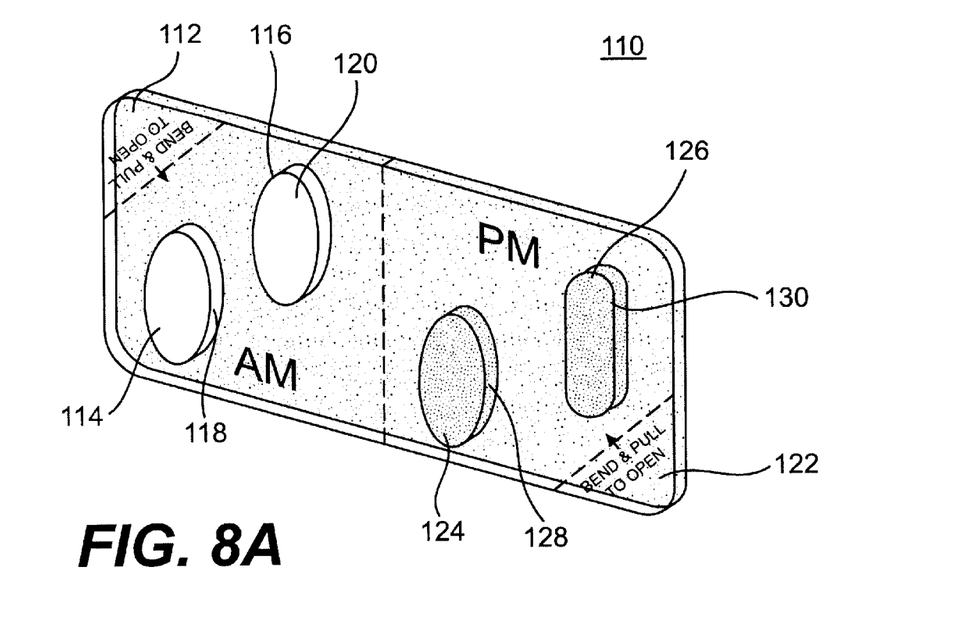
FIG. 8A is a perspective view of an alternate embodiment of the disposable dispensing apparatus, showing alignment of a soft gelatin capsule and a tablet for simultaneous administration according to an embodiment of the present inventive subject matter.
Figure 8B:
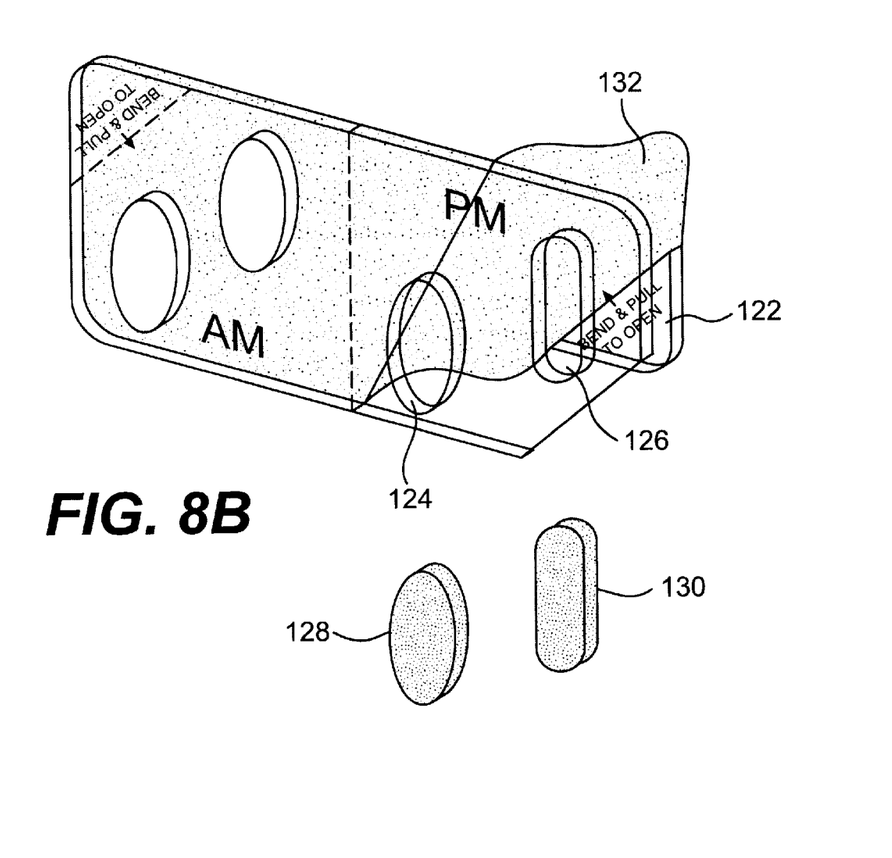
FIG. 8B is a perspective view of an alternate embodiment of the disposable dispensing apparatus with a removable seal being partially removed.

FIGS. 8A and 8B show an alternate embodiment of a novel disposable, dispensing apparatus for providing optimal therapeutic support to an animal by increasing compliance with a complex dosing regimen and facilitating simultaneous administration of storage-incompatible substances.

Shown in FIG. 8A is a perspective view of a blister pack 110. Blister pack 110 is divided into an AM section for morning dosages and a PM section for evening dosages.

The AM section of blister pack 110 has a tab 112 and two recesses 114 and 116. Within recess 114 is a tablet 118 made up of a biologically-active substance and within recess 116 is a tablet 120 also made up of a biologically-active substance. The biologically-active substance of tablet 118 is storage-incompatible with the biologically-active substance of tablet 120. Therefore, by storing tablets 118 and 120 in separate recesses 114 and 116, respectively, the biologically-active storage-incompatible substances of tablets 114 and 116 are prevented from interacting with one another.

The PM section of blister pack 110 has a tab 122 and two recesses 124 and 126. Within recess 124 is a tablet 128 made up of a biologically-active substance and within recess 126 is a soft gelatin capsule 130 also made up of a biologically-active substance. The biologically-active substance of tablet 128 is storage-incompatible with the biologically-active substance of soft gelatin capsule 130. Therefore, by storing tablet 128 and soft gelatin capsule 130 in separate recesses 124 and 126, respectively, the biologically-active storage-incompatible substances of tablet 128 and soft gelatin capsule 130 are prevented from interacting with one another.

FIG. 8B shows blister pack 110 with a removable seal 132 partially removed through the use of tab 122 located at an edge of blister pack 110. After removable seal 132 is removed tablet 118 and soft gelatin capsule 120 can be removed from recesses 114 and 116 respectively.

The disposable, dispensing apparatus may be arranged in a wide variety of configurations, without limitation. Generally, the apparatus contains a blister pack having at least one row of a plurality of predetermined areas, each area defining at least one recess. Any suitable blister pack arrangement may be used provided it contemplates ease of simultaneous administration of components which may not be in direct contact for long-term storage. Thus, each recess is designed to hold only one dosage unit having either only one biologically-active substance or multiple storage-compatible substances.

Each predetermined area may have an independently removable or breakable seal. Once sealed, each recess is moisture resistant, especially important in protecting substances manufactured by freeze-drying or lyophilization. The independent seals allow the sealed surfaces of the predetermined areas to be individually bent and weakened so that contents of one area may be easily obtained without disturbing the sealed surface of adjacent areas. At the same time, the apparatus is sturdy enough to protect the contents from physical stresses, especially those incident to transportation.

The blister packs of the present inventive subject matter may be made by techniques well known and readily available to persons of ordinary skill in the art. Various types of blister packs may be used, without limitation. For example, one type of blister pack that may be used is the push-through pack. Push-through packs are, for example such that the lid material is of aluminum foil or an aluminum foil laminate. Aluminum foil is a preferred material for the lids on blister packs as the thickness of the material employed requires relatively little force for it to rupture. Consequently, the energy for penetration is low and the aluminum exhibits essentially no elasticity. The base of the blister pack may be made of plastic, for example, plastics such as PVC, polyamides, polyolefins, polyesters and laminates or multi-layered materials containing at least one of these materials and, if desired, also containing an aluminum foil. Other blister packs feature a base which is covered by a lid foil. The lid foil may cover the whole of the base area and is usefully provided with a line of weakness in the region of each recess, or each recess may be covered with an individual lid segment. Within the line of weakness or on each lid segment may be a tab for gripping which enables the individual recess to be exposed by pooling back the lid segment. The base and the lid may be may of any of the above materials, whereby plastic laminates may also be employed for the lid materials.

The bases of the present blister packs may be made embossed, cast deep drawn or vacuum formed bases out of plastic, plastic laminates, plastic/paper laminates or plastic/ metal foil laminates. Non-limiting exemplary suitable plastics for bases are films and film laminates containing PVC, polyamides, polyolefins, polyesters, polycarbonates and combinations thereof. The bases may also feature a barrier layer against gases and vapors. Such barrier layers may be a metal foil such as an aluminum foil embedded in a plastic laminate or usefully ceramic layers or metallic layers embedded between two plastic layers. Ceramic layers may be produced by evaporating metals, oxides or nitrides of aluminum, silicon and other metals and semimetals in vacuum and depositing the substances on a plastic substrate. The methods are known as chemical vapor deposition and physical vapor deposition or sputtering. The ceramic layers may be preference contain aluminum oxides or silicon oxides or may be mixtures of various oxides, if desired also mixed with metals such as silicon or aluminum. Metal layers may be created by evaporating metals in vacuum and depositing the metals on a plastic substrate; aluminum layers may be mentioned here by way of example. The plastic substrate may be a plastic film or a plastic base made of the above mentioned plastics. As a rule the lid material for the push-through pack is an aluminum foil or a laminate containing aluminum foil. It has also been proposed to replace the aluminum foil with a plastic that exhibits low elasticity and poor stretching properties. Such plastics may be obtained when large amounts of filler materials are added to the plastic. This last mentioned version would make it possible to obtain easily sorted waste material, for example, no mixture of metal and plastics. Plastics and plastic laminates could also be employed for blister packs with peel back lid material.

The bases usually feature between 4 and 28 recesses in the form of cups or dishes, without limitation. The recesses may be surrounded by a shoulder, said shoulders together forming an interconnected flat plane. The bases are prepared, for example, as an endless strip with the contents in recesses and brought together with the lid material, in particular in lid foil form, likewise in the form of an endless strip. The lid foil covers the base completely and, for example, by sealing or adhesive bonding is jointed to the base at the shoulders. The lid foil may be sealed or adhesively bonded to the shoulders over the whole area or, by choosing a special sealing tool or bonding pattern for the purpose, this sealing or bonding may be only partial. Next, for example, the endless strip of each lidded base part may be cut to the desired size. This may be performed, for example using a stamping tool. At the same time, the blister pack may have outer contours, or it is possible to provide weaknesses in the lid material or the base in order to allow the blister pack to be bent or to create lid segments, making easy removal of the lid segment and removal of the contents possible.

Any dosage form, and combinations thereof, are contemplated by the invention. Examples of such dosage forms include, without limitation, chewable tablet, quick dissolve tablet, effervescent tablet, reconstitutable powder, elixir, liquid, solution, suspension, emulsion, tablet, multi-layer tablet, bi-layer tablet, capsule, soft gelatin capsule, hard gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, dragee, ampoule, ingestible, injectable, infusion, health bar, liquid, food, nutritive food, functional food, yogurt, gelatin, cereal, cereal coating, animal feed or combinations thereof. The preparation of any of the above dosage forms may be performed by techniques and methods well known and readily available to persons of ordinary skill in the art.

Day indicia are incorporated into the blister pack of the present invention. The day indicia may be of various types, without limitation. The day indicia correspond to at least two distinct recesses. For example, without limitation, the day indicia ray be a specific day of the week, such as Monday, Tuesday, Wednesday, Thursday, Friday, Saturday, Sunday or an abbreviation of said day, a specific date or a general succession of days, such as day 1, day 2, day 3, and the like. Day indicia may be indicated directly on the dosage units or on another portion of the blister pack.

Time indicia may be incorporated into the blister pack of the present invention. The time indicia may be of any type, without limitation. The time indicia correspond to at least two distinct time periods, but may correspond to any number of distinct time periods without limitation. For example, without limitation, the time indicia may indicate a general time of the day corresponding to each of said predetermined areas or a specific time of the day corresponding to each of said predetermined areas. Non-limiting exemplary general times of the day may be any of the following: AM, PM, morning, afternoon, evening, day, night, daytime, nighttime and combinations thereof. Each separate row or column of the present blister pack may each indicate a time of day, such as indicate AM doses and PM doses of a medicament. Each predetermined area on the present blister pack may be color coded for time indicia. The blister pack may further include a key defining or explaining the color coding. For example, without limitation, the predetermined area containing the dosage forms to be taken in the morning could be yellow, while the predetermined areas containing the dosage forms to be taken in the afternoon could be orange. In addition, the dosage forms may be directly color coded. For example, each dosage form to be administered in the morning could be identified by the color red and dosage forms to be administered at night could be identified by the color blue, without limitation. Further, each individual recess could be individually color coded for time indicia. Each recess may be made of a transparent or translucent material so that the color coding on the dosage unit may be visible while the dosage unit is in the recess. For example, each recess containing AM doses could be colored green and be plainly visible while in the blister pack. Alternatively, the recess could be an opaque shade of color. A color key may be provided on the blister package to indicate which color corresponds with which dosage date or time. The indicia provide a reliable and effective feedback system in that the patient can determine if the proper dosages have been taken on the right days at the right times by comparing the indicia on the package with a calender or clock. The patient can easily determine if a dose has been missed or if more than one dose was inadvertently taken at an improper time.

The dosage units of the present inventive subject matter may comprise any biologically-active substance, without limitation. Preferably, the dosage units of the present invention comprise vitamin A, B vitamins, vitamin C, vitamin D, vitamin E, vitamin K, essential fatty acids, folic acid, iron, calcium, magnesium, potassium, copper, chromium, zinc, molybdenum, iodine, boron, selenium, manganese, derivatives thereof or combinations thereof. Non-limiting exemplary biologically-active substances of the present inventive subject matter may include thiamin, thiamin pyrophosphate, riboflavin, flavin mononucleoride, flavin adenine dinucleotide, niacin, nicotinic acid, nicotinamide, niacinamide, nicotinamide adenine dinucleotide, tryptophan, biotin, pantothenic acid, ascorbic acid, retinol, retinal, retinoic acid, beta-carotene, 1,25-dihydroxycholecalciferol, 7-dehyrdocholesterol, alpha-tocopherol, tocopherol, tocotrienol, menadione, menaquinone, phylloquinone, naphthoquinone, calcium, calcium carbonate, calcium sulfate, calcium oxide, calcium hydroxide, calcium apatite, calcium citrate-malate, calcium gluconate, calcium lactate, calcium phosphate, calcium levulinate, phosphorus, potassium, sulfur, sodium, docusate sodium, chloride, magnesium, magnesium stearate, magnesium carbonate, magnesium oxide, magnesium hydroxide, magnesium sulfate, copper, iodine, zinc, chromium, molybdenum, carbonyl iron, ferrous fumarate, polysaccharide iron, and combinations and derivatives thereof, without limitation. Non-limiting exemplary derivatives of vitamin compounds include salts, alkaline salts, esters and chelates of any vitamin compound.

The dosage units may be prescription or non-prescription substances, without limitation. The prescription substance may be a hormone replacement agent, a contraceptive agent, an osteoporotic agent, a chemotherapeutic agent, an anti-infective agent, an algesic, a steroid, an appetite suppressant, a weight loss agent, a tobacco antagonist, a cholesterol reducer and combinations thereof.

Non-limiting exemplary prescription substances include erythromycin, penicillins, cephalosporins, theophylline, albuterol, terbutaline, diltiazem, propranolol, nifedepine, clonidine, thioridazine, diazepam, meclizine, ergoloid mesylates, chlorpromazine, carbidopa, levodopa, beclomethasone diproprionate, budesonide, dexamehasone, flunisolide, fluticasone proprionate, mometasone furoate, triamcinolone acetonide, beconase, pulmicort, rhinocort, decadron, aerobid/nasolide, flovent/flonase, azmacort, amprenavir, adefovir dipivoxil, zidovudine, azidothymidine, AZT, paclitaxel, cyclophosphamide, teniposide, taxol, cytoxan, vumon, methotrexate, methotrexate, cisplatin, carboplatin, oxaliplatin, platinol, paraplatin, adriamycin, bleomycin, dactinomycin, daunorubicin, doxorubicin, indarubicin, mitomycin, blenoxane, cosmegen, cerubidine, rubex, indamycin, mutamycin, BCNU, streptozocin, vinblastine, thiotepa, conjugated estrogens, esterified estrogens, estropipate, estradiol, ethinyl estradiol, medroxyprogesterone, meprobamate, desogestrel, levonorgestrel, norethindrone, norethindrone acetate, norgestimate, norgestrel, raloxifene, tamoxifen, methyltestosterone, quinapril, losartan, sotalol, alendronate, atorvastatin, colestipol, clofibrate, and combinations thereof.

The non-prescription substance for inclusion in the first or second dosage form can be a vitamin or derivative thereof, or a mineral compound or derivative thereof. The vitamin or mineral compound may be thiamin, thiamin pyrophosphate, riboflavin, flavin mononucleoride, flavin adenine dinucleotide, niacin, nicotinic acid, nicotinamide, niacinamide, nicotinamide adenine dinucleotide, tryptophan, biotin, folic acid, pantothenic acid, ascorbic acid, retinol, retinal, retinoic acid, beta-carotene, 1,25-dihydroxycholecalciferol, 7-dehydrocholesterol, alpha-tocopherol, tocopherol, tocotrienol, menadione, menaquinone, phylloquinone, naphthoquinone, calcium, calcium carbonate, calcium sulfate, calcium oxide, calcium hydroxide, calcium apatite, calcium citrate-malate, calcium gluconate, calcium lactate, calcium phosphate, calcium levulinate, phosphorus, potassium, sulfur, sodium, docusate sodium, chloride, magnesium, magnesium stearate, magnesium carbonate, magnesium oxide, magnesium hydroxide, magnesium sulfate, copper, iodine, zinc, chromium, molybdenum, carbonyl iron, ferrous fumarate, polysaccharide iron, and combinations and derivatives thereof, without limitation. Derivatives of vitamin compounds include salts, alkaline salts, esters and chelates of any vitamin compound, without limitation. The nonprescription substance can also be a herbal compound, herbal extract, derivative thereof or combinations thereof, without limitation.

A first dosage unit is arrayed on the blister pack adjacent to a second dosage unit. The first dosage unit and the second dosage unit occupy different recesses of the same predetermined area. The first dosage unit and the second dosage unit are each independently in an oral dosage form. The oral dosage form is preferably a chewable tablet, a quick dissolve tablet, an effervescent tablet, an enteric coated tablet, a hard gelatin capsule, a soft gelatin capsule, reconstitutable powder, a suspension, an elixir, a tablet, a caplet, liquid form and combinations thereof. More preferably, when either the first or second dosage unit is a tablet, the other dosage unit is a soft gelatin capsule. The soft gelatin capsule may contain substances ideally suited for administration in a soft gelatin capsule format, while the tablet contains substances which are ideally administered simultaneously with the substances in the soft gelatin capsule, but which are incompatible with the soft gelatin dosage form, for example, vitamin C, without limitation.

Storage-incompatible substances may be any substances that may not be formulated together in a single dosage unit or stored together in direct contact because the substances will interact in a negative manner and also substances that cannot be formulated together in a single dosage unit because the sum total of the dosage amounts of the substances would result in a single dosage unit which is too large to be swallowed. Storage-incompatible substances also include those substances which may be stored in direct contact, however, one of the substances is preferably formulated in a dosage form which is either not preferred or incompatible with the other substance. The storage-incompatible substances may include any storage-incompatible substances, without limitation.

For example, the storage incompatible substances may be hydrophobic compounds and hydrophilic compounds, olefinic compounds and non-olefinic compounds, pH sensitive compounds and non-pH sensitive compounds, substances requiring an anhydrous environment and substances requiring a non-anhydrous environment, acidic drugs and basic drugs, effervescent tablets and high water content drugs or dosage forms, gelatin capsules and aldehydes, quaternary ammonium compounds and anionic substances or any combination of the above.

Non-limiting exemplary storage incompatible substances include, without limitation, ascorbic acid and aluminum hydroxide, ascorbic acid and sodium bicarbonate, citric acid and sodium carbonate, folic acid and calcium carbonate, activated charcoal and amyl nitrate, gelatin capsules and formaldehyde, gelatine capsules and gluteraldehyde, konicin chloride and soap, etylpyridinium chloride and sodium stearate, and combinations thereof.

The predetermined areas are arranged such that the first dosage unit and second dosage unit may be easily removed together and administered together. The concurrent administration may be facilitated in a wide variety of ways. For example, without limitation, the concurrent administration may be facilitated by close proximity of the first and second dosage units on the blister pack, by indicia which indicated both are to be concurrently administered, by a safety seal which makes the two dosage units concurrently available, by a means for simultaneously releasing or forcing both dosage units from the blister pack or any combination of the above.

Each predetermined area is visibly marked by at least one line defining the adjacent predetermined area. This line can be perforated. Where the blister pack contains more than one predetermined area, one or more predetermined areas may contain substances which are storage compatible, provided at least one predetermined area on the blister pack contains storage-incompatible substances in separate recesses.

The apparatus may further comprise a container for receiving and storing the blister pack. The container is divided into a plurality of discrete compartments. At least one compartment is for receiving and storing the blister pack and at least one compartment is for receiving and storing a loose or unpackaged dosage form. The present apparatus can be configured in a sheet formation, rolled formation, multidimensional formation or any other formation.

The present apparatus and method may incorporate uneven or unequal dosing of substances throughout a daily or twenty four hour period of time. For example, the blister pack may provide one amount of a particular vitamin for administration in the morning and a different amount of that same vitamin for administration in the evening. Moreover, the types of substances in the morning and evening need not be the same. Usage of substances may be alternating, for example, without limitation, in every other administration, the dosage amount of a particular vitamin may be the same, or in every other administration, the absence or presence of a particular vitamin alternates. Usage of substances may be progressive, for example, without limitation, increasing amounts of a certain compound may be provided for administration throughout the course of the regimen.

The method and apparatus of the present inventive subject matter may be used by any human or other animal. The present method and apparatus is particularly suitable for individuals with special therapeutic needs or specific therapeutic needs, particularly where those needs would benefit from a complex therapeutic regimen. For example, without limitation, the present method and apparatus is particularly suitable for menopausal women, lactating women, pregnant women, men or women planning to conceive a child, individuals suffering from a pathological condition or any combination of the above.

The present inventive subject matter includes a method for providing optimal therapeutic support to an animal by increasing compliance with a complex dosing regimen and facilitating simultaneous administration of storage-incompatible substances. The present inventive subject matter also encompasses a method for increasing patient compliance with prescription therapeutic substances. The methods of the invention comprise, first, providing a blister pack having at least one row of a plurality of predetermined areas. Preferably, each predetermined area has a seal that is independently accessible, removable or breakable. Each row may also have a seal that is independently accessible, removable or breakable. The methods may involve providing a first dosage unit containing a nonprescription substance in a recess in one predetermined area. The nonprescription substance may be a therapeutic agent. The therapeutic agent may be thiamin, thiamin pyrophosphate, riboflavin, flavin mononucleotide, flavin adenine dinucleotide, niacin, nicotinic acid, nicotinamide, niacinamide, nicotinamide adenine dinucleotide, tryptophan, biotin, pantothenic acid, ascorbic acid, retinol, retinal, retinoic acid, beta-carotene, 1,25-dihydroxycholecalciferol, 7-dehyrdocholesterol, alpha-tocopherol, tocopherol, tocotrienol, menadione, menaquinone, phylloquinone, naphthoquinone, calcium, calcium carbonate, calcium sulfate, calcium oxide, calcium hydroxide, calcium apatite, calcium citrate-malate, calcium gluconate, calcium lactate, calcium phosphate, calcium levulinate, phosphorus, potassium, sulfur, sodium, docusate sodium, chloride, magnesium, magnesium stearate, magnesium carbonate, magnesium oxide, magnesium hydroxide, magnesium sulfate, copper, iodine, zinc, chromium, molybdenum, carbonyl iron, ferrous fumarate, polysaccharide iron, linolenic acid, linoleic acid, docosahexanoic acid, arachidonic acid and combinations and derivatives thereof, without limitation. Non-limiting exemplary derivatives of vitamin compounds include salts, alkaline salts, esters and chelates of any vitamin compound.

The methods may also comprise providing a second dosage unit containing a prescription therapeutic substance in a recess in the blister pack such that the second dosage is located adjacent to the first dosage. The prescription substance may be, without limitation, a hormone replacement agent, a contraceptive agent, an osteoporotic agent, a chemotherapeutic agent, an anti-infective agent, an analgesic, a steroid, an appetite suppressant, a weight loss agent, a tobacco antagonist, an cholesterol reducer or combinations thereof. The prescription therapeutic substance may be a therapeutic regimen is a complex daily therapeutic regimen.

One or more blister packs within the stated parameters may be housed in a suitable dispensing box along with printed material and/or audio/visual aids to assist in compliance with said blister pack.

The methodology of the present inventive subject matter is not strictly limited to blister packs. Any conventional pharmaceutical container(s) having structural similarity to blister packs are suitable. Non-limiting exemplary containers include bottles, vials, tubes, canisters, packets and the like.

The invention being thus described, it will be apparent that the same may be varied in many ways. Such variations are not to be regarded as a departure from the spirit and scope of the invention, and all such modifications are intended to be within the scope of the appended claims. component which at lower doses may be a non-prescription drug or a drug which is available by prescription, without limitation.

The methods of the invention also comprise providing indicia on the blister pack corresponding to the first and second dosage units. Additionally, the indicia provide a reliable and effective feedback system in that the patient can determine if the proper dosages have been taken on the proper days and at the proper times by comparing the indicia on the package with a calender or clock. The patient can easily determine if a dose has been missed or if more than one dose was inadvertently taken at an improper time.

The methods of the invention comprise administering storage-incompatible substances and/or prescription and non-prescription therapeutic substances together from the blister pack to an animal at the time indicated by the indicia. The method of the invention involves a therapeutic regimen. Preferably, the therapeutic regimen is a daily therapeutic regimen. More preferably, the

We claim:

1. A disposable dispensing apparatus for providing optimal therapeutic support to an animal by increasing compliance with a complex dosing regimen and facilitating simultaneous administration of storage-incompatible substances, said apparatus comprising:

a blister pack having a plurality of predetermined areas, each of said predetermined areas defining at least a first recess and a second recess, the first and second recesses each defining a separate area for storing incompatible substances, the incompatible substances being selected from the group consisting of hydrophobic compounds and hydrophilic compounds, olefinic compounds and non-olefinic compounds, pH sensitive compounds and non-pH sensitive compounds, substances requiring an anhydrous environment and substances requiring a non-anhydrous environment, acidic drugs and basic drugs, effervescent tablets and high water content drugs or dosage forms, gelatin capsules and aldehydes, guarternary ammonium compounds and anionic substances, and combinations thereof, respectively;

a first dosage unit occupying the first recess, said first dosage unit comprising a first biologically-active substance;

a second dosage unit occupying the second recess, said second dosage unit comprising a second biologically-active substance;

wherein the complex dosing regimen requires simultaneous administration of said first and second biologically-active substances; said first biologically-active substance being storage incompatible with said second biologically-active substance; and wherein said first recess and said second recess provide shelf stability by independently isolating in close proximity said first dosage unit and said second dosage unit to prevent interaction between the first and second biologically-active substances while facilitating simultaneous administrations of said substances.

2. The apparatus of claim 1, further comprising a day indicia provided on said blister pack, said day indicia corresponding to each of said predetermined areas to increase patient compliance with said complex dosing regimen by indicating which day the dosage units are to be administered.

3. The apparatus of claim 1, wherein each of said predetermined areas has a seal that is independently accessible, removable or breakable.

4. The apparatus of claim 3, wherein said seal is a safety seal.

5. The apparatus of claim 3, wherein said seal is a pull-tab.

6. The apparatus of claim 5, wherein said pull-tab bears a time indicia.

7. The apparatus of claim 1, wherein said apparatus further comprises time indicia provided on said blister pack indicating a general time of the day corresponding to each of said predetermined areas.

8. The apparatus of claim 7, wherein said time indicia is color coded.

9. The apparatus of claim 7, wherein said general time of the day is selected from the group consisting of AM, PM, morning, afternoon, evening, day, night, daytime, nighttime and combinations thereof.

10. The apparatus of claim 1, wherein said apparatus indicates a time AM which is aligned with a first column of a plurality of said predetermined areas, and wherein said apparatus indicates a time PM which is aligned with a second column of a plurality of said predetermined areas.

11. The apparatus of claim 10, wherein the first dosage unit of each of said predetermined areas in said first column and the first dosage unit of each of said predetermined areas in said second column contain different types or uneven amounts of biologically-active substances.

12. The apparatus of claim 1, wherein each of said predetermined areas is visibly marked by at least one line defining an adjacent predetermined area.

13. The apparatus of claim 1, wherein each of said predetermined areas is defined by at least one perforated line demarcating that area from an adjacent predetermined area.

14. The apparatus of claim 1, wherein the blister pack comprises more than one row of said plurality of predetermined areas.

15. The apparatus of claim 1, wherein the first recess contains a soft gelatin capsule and wherein the second recess contains a tablet.

16. The apparatus of claim 1, wherein said first biologically-active substance is a hydrophobic compound and said second biologically-active substance is a hydrophilic compound.

17. The apparatus of claim 1, wherein said first biologically-active substance is an olefinic compound and said second biologically active substance is a non-olefinic compound.

18. The apparatus of claim 1, wherein said first biologically-active substance is a pH sensitive compound and said second biologically-active substance is a non-pH sensitive compound.

19. The apparatus of claim 1, wherein said first biologically-active substance requires an anhydrous environment and said second biologically-active substance requires a non-anhydrous environment.

20. The apparatus of claim 1, wherein said first and second biologically-active substances are independently selected from the group consisting of vitamin A, B vitamins, vitamin C, vitamin D, vitamin E, vitamin K, essential fatty acids, folic acid, iron, calcium, magnesium, potassium, copper, chromium, zinc, molybdenum, iodine, boron, selenium, manganese, derivatives thereof and combinations thereof.

21. The apparatus of claim 1, wherein said first and said second biologically active substance are independently selected from the group consisting of thiamin, thiamin pyrophosphate, riboflavin, flavin mononucleoride, flavin adenine dinucleotide, niacin, nicotinic acid, nicotinamide, niacinamide, nicotinamide adenine dinucleotide, tryptophan, biotin, pantothenic acid, ascorbic acid, retinol, retinal, retinoic acid, beta-carotene, 1,25-dihydroxycholecalciferol, 7-dehydrocholesterol, alpha-tocopherol, tocopherol, tocotrienol, menadione, menaquinone, phylloquinone, naphthoquinone, calcium, calcium carbonate, calcium sulfate, calcium oxide, calcium hydroxide, calcium apatite, calcium citrate-malate, calcium gluconate, calcium lactate, calcium phosphate, calcium levulinate, phosphorus, potassium, sulfur, sodium, docusate sodium, chloride, magnesium, magnesium stearate, magnesium carbonate, magnesium oxide, magnesium hydroxide, magnesium sulfate, copper, iodine, zinc, chromium, molybdenum, carbonyl iron, ferrous fumarate, polysaccharide iron, linoleic acid, linolenic acid, docosahexanoic acid, arachidonic acid and combinations and derivatives thereof.

22. The apparatus of claim 1, wherein said first and second biologically-active substance are independently a vitamin compound or derivative thereof.

23. The apparatus of claim 1, wherein said first dosage unit and said second dosage unit are each in a dosage form independently selected from the group consisting of oral, buccal, sublingual, rectal, parenteral, topical, inhalational, injectable and transdermal.

24. The apparatus of claim 23, wherein said oral dosage form is selected from the group consisting of a chewable tablet, a quick dissolve tablet, an effervescent tablet, a hard gelatin capsule, a soft gelatin capsule, a reconstitutable powder, a suspension, an elixir, a tablet, a caplet and combinations thereof.

25. The apparatus of claim 1, wherein said day indicia is color coded.

26. The apparatus of claim 1, wherein said apparatus further comprises a container for receiving and storing said blister pack.

27. The apparatus of claim 26, wherein said container is divided into a plurality of discrete compartments and wherein at least one compartment is for receiving and storing said blister pack and at least one compartment is for receiving and storing a loose or unpackaged dosage form.

28. The apparatus of claim 1, wherein said blister pack comprises more than one row of said plurality of predetermined areas.

29. The apparatus of claim 1, wherein said disposable dispensing apparatus is configured in a rolled formation.

30. The apparatus of claim 1, wherein said first and second dosage units are labeled with day indicia and the top of said recess is comprised of a transparent material.

31. The apparatus of claim 1, wherein said first and second dosage units are labeled with time indicia and the top of said recess is comprised of a transparent material.

32. The apparatus of claim 1, further comprising a therapeutic device.

33. The apparatus of claim 1, wherein said therapeutic device is for reducing or eliminating nausea.

34. A storage stable, disposable dispensing apparatus for increasing patient compliance with taking at least one prescription substance through proximity and conjoint accessibility with at least one nonprescription substance, said apparatus comprising:
  a blister pack having at least one row of a plurality of predetermined areas, each area defining at least two recesses, each of the recesses defining a separate area for storing incompatible substances, the incompatible substances being selected from the group consisting of hydrophobic compounds and hydrophilic compounds, olefinic compounds and non-olefinic compounds, pH sensitive compounds and non-pH sensitive compounds, substances requiring an anhydrous environment, and substances requiring a non-anhydrous environment, acidic and basic drugs, effervescent tablets and high water content drugs or dosage forms, gelatin capsules and aldehydes, quarternary ammonium compounds and anionic substances, and combinations thereof, respectively;
  a first dosage unit occupying at least one recess of at least one of said predetermined areas, said first dosage unit containing a prescription substance selected from the group consisting of a hormone replacement agent, a contraceptive agent, an osteoporotic agent, a chemotherapeutic agent, an anti-infective agent, an analgesic agent, a steroid, an appetite suppressant, a weight loss agent, a tobacco antagonist, a cholesterol reducer and combinations thereof;
  a second dosage unit occupying at least one recess of at least one of said predetermined areas, said second dosage unit containing a prescription therapeutic substance, said second dosage unit arrayed with said first dosage unit on said blister pack adjacent to said second dosage unit;
  a day indicia provided on said blister pack, said day indicia corresponding to at least one of said predetermined areas;
  wherein each of said predetermined areas has a seal that is independently accessible, removable or breakable; and
  wherein said disposable dispensing container apparatus is stored in a storage container, wherein said container is divided into a plurality of discrete compartments and wherein at least one compartment is for receiving and storing said blister pack and at least one compartment is for receiving and storing a loose or unpackaged dosage form.

35. A disposable dispensing apparatus for providing optimal therapeutic support to an animal by increasing compliance with a complex dosing regimen and facilitating administration of uneven doses of a biologically-active substance, said apparatus comprising:
  a blister pack having at least two rows of a plurality of predetermined areas;
  a first row of predetermined areas, each of the predetermined areas defining a first recess adapted to receive a first dosage unit, said first row of predetermined areas having a first time indicia;
  a second row of predetermined areas, each of the predetermined areas defining a first recess adapted to receive a second dosage unit, said second row of predetermined areas having a second time indicia; and
  wherein the first dosage unit has a greater or lesser amount by weight of the biologically active than the second dosage unit.

36. The apparatus of claim 35, further comprising a day indicia provided on said blister pack, said day indicia corresponding to each of said predetermined areas to increase patient compliance with said complex dosing regimen by indicating which day the dosage units are to be administered.

37. The apparatus of claim 36, wherein said day indicia is Monday, Tuesday, Wednesday, Thursday, Friday, Saturday, Sunday, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, One, Two, Three, Four, Five, Six, Seven, Eight, Nine, Ten, Eleven, Twelve, Thirteen, Fourteen, Fifteen, Sixteen, Seventeen, Eighteen, Nineteen, Twenty, Twenty One, Twenty Two, Twenty Three, Twenty Four, Twenty Five, Twenty Six, Twenty Seven, Twenty Eight, Twenty Nine, Thirty, Thirty One, January, February, March, April, May, June, July, August, September, October, November, December and combinations thereof.

38. A method for providing optimal therapeutic support to an animal by increasing compliance with a complex dosing regimen and facilitating simultaneous administration of storage-incompatible substances, which comprises:
  providing a blister pack having a plurality of predetermined areas, each of said predetermined areas defining at least a first recess and a second recess;
  providing a first dosage unit occupying the first recess, said first dosage unit comprising a first biologically-active substance;
  providing a second dosage unit occupying the second recess, said second dosage unit comprising a second biologically-active substance;
  providing day indicia on said blister pack, said day indicia corresponding to each of said predetermined areas to increase patient compliance with said complex dosing regimen by indicating which day the dosage units are to be administered;
  administering a nonprescription therapeutic substance and a prescription therapeutic substance together from said blister pack to an animal when indicated by said day indicia;

wherein the complex dosing regimen requires simultaneous administration of said first and second biologically-active substances; said first biologically-active substance being storage-incompatible with said second biologically-active substance; and wherein said first recess and said second recess provide shelf stability by independently isolating in close proximity said first dosage unit and said second dosage unit to prevent interaction between the first and second biologically-active substances while facilitating simultaneous administration of said substances.

39. The method of claim 38, wherein said animal is a pregnant woman.

40. The method of claim 38, wherein said animal is a lactating woman.

41. The method of claim 38, wherein said animal is a menopausal woman.

42. The method of claim 38, wherein said animal is a man or woman preparing to conceive a child.

43. A method for providing optimal therapeutic support to an animal by increasing compliance with a complex dosing regimen and facilitating administration of uneven doses of at least one biologically-active substance, which comprises:

providing the biologically-active substance in a blister pack having a first row of a plurality of predetermined areas and a second row of a plurality of predetermined areas; each predetermined area of the first row defining a recess for receiving a first dosage unit and each predetermined area of the second row receiving a second dosage unit;

wherein the first row of predetermined areas corresponds to a first time indicia and the second row of predetermined areas corresponds to a second time indicia;

a second row of predetermined areas, each of the predetermined areas defining a first recess adapted to receive a second dosage unit, said second row of predetermined areas having a second time indicia; and wherein the first dosage unit and the second dosage unit contain uneven amounts of the biologically-active substance.

44. The method of claim 43, wherein said blister pack has a day indicia corresponding to each of said predetermined areas to increase patient compliance with said complex dosing regimen by indicating which day the dosage units are to be administered.

* * * * *